United States Patent
Mandal et al.

(10) Patent No.: US 6,693,177 B1
(45) Date of Patent: Feb. 17, 2004

(54) PROCESS FOR PREPARATION OF A BIOMARKER SPECIFIC FOR O-ACETYLATED SIALIC ACID USEFUL FOR DIAGNOSING, MONITORING TREATMENT OUTCOME, AND PREDICTING RELAPSE OF LYMPHOBLASTIC LEUKEMIA

(76) Inventors: Chitra Mandal, Indian Institute of Chemical Biology, 4 Raja S.C. Mullick Road, Jadavpur, Calcutta (IN), 700 032; Santanu Pal, Indian Institute of Chemical Biology, 4 Raja S.C. Mullick Road, Jadavpur, Calcutta (IN), 700 032; Mitali Chatterjee, Indian Institute of Chemical Biology, 4 Raja S.C. Mullick Road, Jadavpur, Calcutta (IN), 700 032

(*) Notice: Subject to any disclaimer, the term of this patent is extended or adjusted under 35 U.S.C. 154(b) by 0 days.

(21) Appl. No.: 09/453,555

(22) Filed: Dec. 3, 1999

(30) Foreign Application Priority Data

Sep. 8, 1999 (IN) ........................................ 1192/DEL/99

(51) Int. Cl.⁷ .......................... C07K 1/00; C07K 16/00; A61K 49/00; G01N 33/574
(52) U.S. Cl. .......................... 530/413; 436/64; 424/9.1; 530/387.5; 435/7.23
(58) Field of Search .......................... 630/387.1, 387.5, 630/387.7, 412, 413; 435/7.1, 7.2, 7.21, 7.23; 436/64, 501; 424/9.1

(56) References Cited

PUBLICATIONS

Siebert, H.–C. et al. Molecular dynamics–derived conformation and intramolecular interaction analysis of the N–acetyl–9–O–acetylneuraminic acid–containing ganglioside GD1a and NMR–based analysis of its binding to a human polyclonal immunoglobulin G fract.*

Mandal, C. et al. O–Acetyl sialic acid binding lectin as a probe for detection of subtle change on cell surface induced during acute lymphoblastic leukemia (ALL) and its clinical application. Indian Journal Biochemistry & Biophysics, 34: 82–86, 1997.*

* cited by examiner

Primary Examiner—Anthony C. Caputa
Assistant Examiner—Gary B. Nickol
(74) Attorney, Agent, or Firm—Mishrilal Jain, Esq.; Nirmel & Associates

(57) ABSTRACT

The invention relates to a novel process for preparation of a biomarker specific for O-acetylated sialic acid and useful for the diagnosis, monitoring outcome of treatment and prediction of relapse of acute lymphoblastic leukemia, said process comprising the steps of (I) separating serum from the blood of patients of acute lymphoblastic leukemia; (ii) separation of low molecular weight fractions and galactose binding proteins from the serum on affinity matrix; (iii) passing the galactose free protein fraction obtained in step (ii) over another affinity matrix to capture O-acetyl sialic acid specific protein fraction; (iv) eluting specific protein fraction with a buffer at alkaline pH in the range of 8.0–11.0 followed by immediate neutralization of the fraction; (v) passing O-acetyl sialic acid specific protein obtained in step (iv) over Agarose column to get O-acetyl sialic acid specific antibody and eluting the said antibody with an appropriate buffer at acidic pH, followed by immediate neutralization of the fraction and dialyzing the neutralized protein to get purified disease specific antibody as biomarker and a method of diagnosing, monitoring outcome of treatment and prediction of relapse of acute lymphoblastic leukemia using the biomarker obtained by the novel process.

13 Claims, No Drawings

PROCESS FOR PREPARATION OF A BIOMARKER SPECIFIC FOR O-ACETYLATED SIALIC ACID USEFUL FOR DIAGNOSING, MONITORING TREATMENT OUTCOME, AND PREDICTING RELAPSE OF LYMPHOBLASTIC LEUKEMIA

FIELD OF THE INVENTION

The present invention relates to a novel process for the preparation of a biomarker which is an antibody for O-acetylated sialic acid and useful for the diagnosis, monitoring outcome of treatment and prediction of relapse of acute lymphoblastic leukemia. More particularly, the present invention relates to a novel process for the preparation of O-acetylated sialic protein immunoglobin useful as a biomarker for the diagnosis of acute lymphoblastic leukemia.

BACKGROUND OF THE INVENTION

Leukemia is a heterogeneous group of neoplastic cells arising from the malignant transformation of hematopoietic (i.e. blood forming) cells. Leukemia can be broadly classified according to the cell type involved myeloid or lymphoid and as acute and chronic depending on the natural history of the disease. Acute lymphoblastic leukemia (ALL) is the commonest type of leukemnia in children and adolescents. It occurs in all races with a peak incidence in children between 3 and 5 years of age. ALL is diagnosed in 2000–3000 new cases of children in the United States every year, whereas acute myelogenous leukemia is diagnosed in only 500 children and chronic myeloid leukemia in fewer than 100. About 40 million children under the age group of 15 years are affected and nearly about 75% of these have ALL. Pediatric hematopoietic malignancies rank first in cancer incidence and mortality in children and are responsible for roughly 40% of childhood related death.

The causes of leukemia are not known but environmental agents including irradiation, chemical carcinogens, cytogenetic abnormalities and retrovirus infections are known to play an important role in the etiology of leukemia. For instance, individual with occupational radiation exposure, patients receiving radiation therapy or Japanese survivors of the atomic bomb explosions have a predictable and dose related increased incidence of leukemia.

For oncologists, acute lymphoblastic leukemia (ALL) represents a major therapeutic success as this can be achieved in nearly 65% of patients (Pui C H, Crist W M Jr. Current Opinion in Oncology, Vol 7, p 36, 1995 and Pui C H, Crist W M Jr. Lancet, Vol 347, p1783, 1996). However, relapse and eventually treatment failure occurs in many cases receiving identical treatment and this area is a major challenge for leukemia specialists (Pui C H, Crist W M Jr. New England Journal of Medicine, Vol 332, p1618, 1995).

At the time of diagnosis, the leukemic cell mass is usually between $10^{11}$–$10^{12}$ cells and available chemotherapeutic agents produce a fractional cell kill capable of 3 to 5 log kill resulting in the elimination of 99.99 to 99.999% of leukemic cells. The persistence of the remaining 0.01 to 0.001% leukemic cells tantamounts to the persistence of $10^8$ to $10^9$ cells respectively (Champlin and Golde, Harrison Textbook of Internal Medicine pg 1552). What is important is these persisting leukemic cells are not detectable by standard morphology in bone marrow or peripheral blood. It is these cells that are responsible for relapse, if post induction chemotherapy fails to eradicate them. To eliminate this non-detectable yet existing leukemic cell mass, maintenance therapy is given for an extended period (2–2.5 years) for preventing relapse by eradicating this "ice berg" like leukemic cell and reducing and possibly eradicating blast cells. This "ice berg" is conventionally addressed as "Minimal Residual Disease" (MRD) (Knechtli et. Al. J. Clin. Path. 48,1995). MRD is defined as the presence of leukemic cells not detectable by morphology. Despite advances in the treatment of childhood ALL, the risk of relapse remains about 30 percent as patients in remission may harbor residual leukemic blasts, the cause of disease persistence and resurgence is referred to as minimal residual disease, MRD. If the detection of residual leukemia is to be used in clinical practice, the analysis should be performed as early as possible and the laboratory technique should be simple and rapid so that treatment can be tailored to the adjusted assessment of risk. Assays to detect residual blast cells is the need of the hour as these will help the clinician to assess the effect of treatment on tumor burden and allow anticipation of relapse with greater precision (Brisco M J, Condan J, Hughes E, et al. Lancet, Vol 343, p196, 1994).

Currently no specific marker is available to pinpoint the dose of chemotherapy and duration of maintenance therapy in acute lymphoblastic leukemia. Existing methods for the detection of leukemia blast cells are i) cytomorphology and karyotyping ii) immunological methods iii) molecular detection.

Cytomorphology and karyotyping: Acquired non-random chromosomal translocation occur in 30–70% of ALL patients and can serve as marker of disease. But the approach has limited sensitivity (1–5%) primarily due to the paucity of leukemic cells during clinical remission (Campana D, Pui C H, Blood, Vol 85, p1416, 1995). Fluorescent in situ hybridization using chromosome specific or locus specific probes allow identification of abnormalities in cells at metaphase (Le Beau M M, Blood, Vol 81, p1979, 1993). However, sensitivity remains at 1% level.

Immunological Methods: Immunological methods based on the recognition of leukemia associated phenotypes not usually found in normal bone marrow have had promising results (Cole et al. Baillieres din Haematol. 7, 183, 1994). Immunophenotyping has been complemented by flow cytometric analysis where a combination of markers have been able to quantify MRD with a sensitivity usually in the order of $10^2$ to $10^3$ which is inferior to available DNA based method (Hun & Andreef 8, 713, 1994).

Molecular approaches: In majority of the cases, relapse of acute lymphoblastic leukemia is thought to involve the same leukemic clone as the original disease (Bunin N J et al, Leukemia, Vol 4, p727, 1990). Around 80% of cases of childhood acute lymphoblastic leukemia are due to clonal expansion of precursor B cells and have rearrangement of lgH gene, from which specific DNA probes have been generated. Several PCR methods (Brisco M J. Condan J, Hughes E, Lancet, Vol 343, p196, 1994: Veelken H. Tyeko B. Sklar J., Blood. Vol 78, p1318, 1991; Wasserman R. Galili N. I to J. et al., Journal of Clinical Oncology, Vol 10, p1879, 1992) have been reported for detection of MRD in childhood acute lymphoblastic leukemia. This technique detects leukemia specific DNA sequences such as fusion regions of immunoglobulin (Ig) and TcR genes with a sensitivity of $10^5$ for the detection of residual disease in childhood acute lymphoblastic leukemia. All these published methods are successful in only half of the patients since different individuals show different rearrangement of immuloglobulin genes or T cell receptor genes.

The principal drawbacks of the PCR methods for routine follow up of the patients are (i) occurrence of false positive results due to contamination of reaction mix with previously employed samples (ii) occurrence of false negative results owing to degraded RNA or DNA or clonal evolution in approximately 20% of cases (iii) not all leukemic specific gene rearrangements are amenable to initial amplification of PCR using universal primers (iv) a heterogeneous distribution of residual leukemic cells may result in sampling error since gene rearrangements may be different in different individuals (v) these methods are costly, lengthy and sophisticated requiring technical expertise. Therefore, the reliability of PCR assays depends on the use of stringent quantitation protocols and analysis of multiple genetic targets to prevent false negative results due to changes in the pattern of gene rearrangement during the disease course. These mandatory technical requirements further complicate an already laborious procedure and also make it expensive thereby limiting its suitability for routine clinical use. Under these circumstances, use of a novel biomarker effectively will serve as an index to reflect the clinical status of individual patients following therapy.

Since the determination of PCR undetectable residual disease is necessary for cures in most patients, it can be proposed that molecular remission, defined as PCR undetectable disease, is a milestone and a target for achieving cure.

In India, the research in the field of acute lymphoblastic leukemia is mainly carried out at the Tata Memorial Hospital, Bombay. Their interest in Acute Lymphoblastic Leukemia (ALL) is focussed on cytogenetics (Gladstone D et. al., Indian Journal of Medical Research, Vol 99, p264, 1994), infection analysis (Raje B et. al. Pediatric Hematology and Oncology, Vol 11, p271, 1994), and central nervous system relapse (Iyer A et. al., Leukemia and Lymphoma, Vol 13, p183, 1994).

Sialic acids are a family of derivatives of N-acetyl or N-glycoyl neuraminic acids and are very important constituents of cell surface architecture. Sialic acids also function as masking agents on antigens, receptors and other recognition sites of the cell surface (Varki A, Glycobiology, Vol. 1, p25, 1992). The O-substituted sialic acids exhibit species and tissue specific distribution in animals (Schauer R, Advanced Carbohydrate Chemistry Biochemistry, Vol. 40, p131, 1982). Changes in sialic acid and the degree of O-acetylation of sialic acid residues have been reported in transformed and malignant cells.

Recently, the applicants exploited the restricted specificity of 9-O-acetylated sialic acid binding lectin, and identified specific biomarkers namely 9-O-acetyl sialoglycoconjugates on lymphoblast of 87 children suffering from ALL. (Sinha D. Mandal C and Bhattacharyya D et al., Leukemia, Vol. 13, p119–125, 1999) and assessed their differential expression at different phases of therapy (Sinha D. Mandal C and Bhattacharyya D. 1999 Leukemia 13 (2) 309–312; Mandal C. Sinha D. Sharma V and Bhattacharyya D. Indian Journal of Biochemistry Biophysics, Vol. 34, p82, 1997). A blood based lymphoproliferative assay to monitor the treatment outcome of ALL patients (n=203) has been successfully developed (Sinha D. Mandal C and Bhattacharyya D. Leukemia Research, 1999 (in press).

In U.S. Pat. No. 5,925,530 the applicants described a lymphoproliferation assay, employing $ATN_H$. It is a simple, blood based assay wherein maximum lymphoproliferative doses are used to determine the expression of 9-OAcSGs which effectively serves as an index to reflect the clinical status of individual patients following the therapy. Although, the lymphoproliferation assay detects lymphoblasts with a sensitivity of $10^4$, use of radioisotopes i.e. $[^3H]$-TdR and elaborate lengthy immunological methods limits its widespread application.

Accordingly, the applicants felt the need to provide a simple and sensitive diagnostic reagent useful in detecting and monitoring treatment outcome of ALL. To this end, the applicants have detected biomarker anti- 9-O-acetylated sialoglycoconjugate antibody with the help of a sialoglycoprotein namely bovine submaxillary mucin and developed a novel BSM-ELISA useful for the detection of minimal residual disease (MRD). Anti-9-O-acetyl sialoglycoconjugates antibodies were detected in the serum lymphoblasts of ALL patients. The invention provides a simpler BSM-ELISA for detection of specific antibodies present in the serum for diagnosis, monitoring and for the prediction of relapse in acute lymphoblastic leukemia (ALL). This biomarker will specially be helpful for the detection of antibodies specific for O-acetylated sialic acid induced on the leukemic blasts and will reflect chemotherapuetic outcome in these children at different clinical stages of the disease. So, this invention provides an indicator as to when and how long should chemotherapy should be continued to predict the probability of relapse. Therefore, this reagent will serve as an effective measure in the battle for monitoring treatment outcome in patients suffering from acute lymphoblastic leukemia.

BSM-ELISA, can be used for (i) diagnosis of both types of acute lymphoblastic leukemia (B & T ALL) as this disease specific antibody circulating in the Patient serum shows binding to both types of cancer cells. (ii) The amount of biomarker specific for O-acetylated sialic acid is determined and has been exploited to correlate the status of patients with regards to their blast cells which stay in peripheral blood even after chemotherapy. (iii) The quantity of biomarker specific for O-acetyalated sialic acid has been established to be directly proportional to presence of leukemic blast cells i.e. cancer cells. Therefore, by measuring the amount of the biomarker in the Patient serum by the immunodetection assay, it is possible to know the status of different stages of diseases. (iv) The correlation with the status of the disease is assessed and it is confirmed that the biomarker i.e. disease specific antibody has both diagnostic and prognostic potential. (v) The immunoglobulin G (IgG) subclass distribution of these antibodies reacting with leukemic blasts having O-AcSA in patients in comparison to normal healthy individuals has been characterized by the ELISA. Amongst the four human IgG subclasses, $IgG_1$ and $IgG_2$ are significantly increased in ALL patients as compared to normal individuals. However, their $IgG_3$ and $IgG_4$ levels are unchanged and comparable to normal healthy individuals. Therefore, measuring both $IgG_1$ and $IgG_2$ specific for O-Acetyl sialic acid in patients by an isotype ELISA is very much beneficial. The disease specific IgM antibody has also been found to be potentially important.

In short, Advantages of BSM-ELISA over U.S. Pat. No. 5,925,530 include:
1. It is a safe, non radiometric assay,
2. Does not need a tissue culture set up,
3. Takes only a few hours in comparison to 4–5 days long laborious work,
4. Requires only Patient's serum samples which can be collected and stored at cold for a long time 0–10 years,
5. Therefore, immediate processing of the patient's blood is not necessary. This is specially helpful for monitoring patients for a long term follow-up (0–5 years),
6. It is not necessary to perform careful laborious immunological method since the disease specific antibody level can be directly read on an ELISA plate reader, 7. Therefore, the overall processing time and labor involved is markedly reduced,
8. Compared to [$^3$H]-TdR uptake, wherein the liquid scintillation counter requires a time of at least one minute to analyze the counts incorporated in each well of the assay plate, BSM-ELISA takes only one minute for 96 wells,
9. Since the BSM-ELISA, unlike lumphoproliferation assay using [$^3$H]-TdR uptake, does not require radioisotopes, scintillation fluid and cell harvester, it has a low cost benefit ratio which is certainly relevant specifically in developing countries.

Furthermore, antibody level shows a good correlation with leukemic blast and therefore, nonradiometric BSM-ELISA assay holds promise as an alternative to evaluating treatment outcome in ALL.

SUMMARY OF THE INVENTION

A main advantage of the present invention is to provide a method for the preparation of antibodies specific for O-acetylated sialic acid, useful for the diagnosis, monitoring outcome of treatment and prediction of relapse of acute lymphoblastic leukemia.

Another advantage of the present invention is to provide a process for the quantification of the anti-antibody specific for O-acetylated sialic acid present in the serum of ALL patient with the help of a simple, specific, sensitive, non-invasive and economical bovine submaxillary mucin ELISA which allows the assessment of the treatment outcome of ALL patients.

Yet another advantage is to provide a method for the diagnosis, monitoring outcome of treatment and prediction of relapse of ALL.

The invention relates to a novel process for preparation of a biomarker specific for O-acetylated sialic acid and useful for the diagnosis, monitoring outcome of treatment and prediction of relapse of acute lymphoblastic leukemia, said process comprising the steps of (I) separating serum from the blood of patients of acute lymphoblastic leukemia; (ii) separation of low molecular weight fractions and galactose binding proteins from the serum on affinity matrix; (iii) passing the galactose free protein fraction obtained in step (ii) over another affinity matrix to capture O-acetyl sialic acid specific protein fraction; (iv) eluting specific protein fraction with a buffer at alkaline pH in the range of 8.0–11.0 followed by immediate neutralization of the fraction; (v) passing O-acetyl sialic acid specific protein obtained in step (iv) over Agarose column to get O-acetyl sialic acid specific antibody and eluting the said antibody with an appropriate buffer at acidic pH, followed by immediate neutralization of the fraction and dialyzing the neutralized protein to get purified disease specific antibody as biomarker and a method of diagnosing, monitoring outcome of treatment and prediction of relapse of acute lymphoblastic leukemia using the biomarker obtained by the novel process.

Additional advantages and novel features of the invention will be set forth in part in the description that follows, and in part will become more apparent to those skilled in the art upon examination of the following or upon learning by practice of the invention.

DETAILED DESCRIPTION

In accordance with the foregoing advantages, the invention provides a process for preparation of O-acetyl specific immunoglobulin protein useful as a biomarker for the diagnosis, monitoring outcome of treatment and prediction of relapse of ALL comprising the steps of:

(i) separating serum from blood collected from patients of acute lymphoblastic leukemia by known methods;
(ii) removing low molecular weight fractions and galactose binding proteins from the serum by column chromatography on affinity matrix;
(iii) collecting unbound fraction from affinity matrix;
(iv) passing the galactose free protein fraction obtained in step (ii) over another affinity matrix to capture O-acetyl sialic acid specific protein fraction;
(v) eluting specific protein fraction with a buffer at alkaline pH in the range of 8.0–11.0 followed by immediate neutralization of the fraction;
(vi) passing O-acetyl sialic acid specific protein obtained in step (iv) over Protein G-agarose or protein A agarose or protein A Sepharose or protein G Sepharose or anti-human immunoglobulin or only IgG/IgM coupled to Sepharose or agarose column to get O-acetyl sialic acid specific antibody i.e. immunoglobulin and eluting the said antibody with a buffer at acidic pH in the range of 2.0–6.5;
(vii) immediate by neutralizing the fraction and subjecting the neutralized protein and dialyzing to get purified O-acetyl specific immunoglobulin protein as disease specific antibody or biomarker.

In an embodiment, a disease specific antibody or immunoglobulin i.e. the biomarker specific for O-acetylated sialic acid is purified from the serum of patients suffering from acute lymphoblastic leukemia at different stages of the disease.

In another embodiment, whole blood is collected in a container in presence or absence of any available anticoagulants such as Elseiver's solution or heparin or dextrose.

In yet another embodiment, blood is incubated for clotting at room temperature for a short period of time or plasma may be collected from blood.

In a further embodiment, nonspecific proteins are removed from specific affinity matrix such as bovine submaxillary mucin—Sepharose 4B by extensive washing of unbound non O-acetyl sialic acid specific fractions with buffer selected from phosphate buffer saline or Tris buffer saline.

In still another embodiment, specific protein is eluted with buffer of alkaline pH in the range of 8.0–11.0 from bovine submaxillary mucin—Sepharose 4B.

In one more embodiment, eluted specific protein is immediately neutralized with sodium acetate or monosodium phosphate for better stability of the eluted protein.

The invention preferably provides a method of diagnosing, monitoring the outcome, treatment and prediction of relapse of acute lymphoblastic leukemia in patients, which method comprises the steps of:

(i) collecting an anticoagulated blood sample from the patient,
(ii) removing low molecular weight fractions and galactose binding proteins from the serum by column chromatography on affinity matrix,
(iii) collecting unbound fraction from affinity matrix,
(iv) passing the galactose free protein fraction obtained in step (ii) over another affinity matrix to capture O-acetyl sialic acid specific protein fraction,
(v) eluting specific protein fraction with a buffer at alkaline pH in the range of 8.0 –11.0 and immediately neutralizing the fraction,
(vi) passing O-acetyl sialic acid specific protein obtained in step (iv) over Protein G—agarose or protein A agarose or protein A Sepharose or protein G Sepharose or anti-human immunoglobulin or only IgG/IgM coupled to Sepharose or agarose column, and (vii) determining the quantity of biomarker specific for O-acetylated sialic acid in the serum of the patient by immunodetection assay in relation to the blast cells in the peripheral blood wherein the quantity of the biomarker is indicative of the different phases or stages of ALL wherein a decrease in the antibody level with the chemotherapeutic response is related directly to the decrease in relapse of the disease.

In the above preferred method, whole blood is collected in a container in presence or absence of any available anticoagulants such as Elseiver's solution or heparin, dextrose.

In another embodiment, blood is incubated for clotting at room temperature for a short period of time or plasma may be collected from blood.

In yet another embodiment, nonspecific proteins are removed from specific affinity matrix such as bovine submaxillary mucin—Sepharose 4B by extensive washing of unbound non O-acetyl sialic acid specific fractions with buffer such as phosphate buffer saline or Tris buffer saline.

In still another embodiment, specific protein is eluted with buffer of alkaline pH in the range of 8.0–11.0 from bovine submaxillary mucin—Sepharose 4B.

In another embodiment, eluted specific protein is immediately neutralized with sodium acetate or monosodium phosphate for better stability of the eluted protein.

In an embodiment, the $IgG_1$ and $IgG_2$ specific for O-Acetyl sialic acid in the patient's serum are determined by an isotype ELISA to diagnose phases or stages of acute lymphoblastic leukemia.

In an embodiment the serum is separated from the blood of patients afflicted with acute lyphoblastic leukemia wherein the blood is collected in the absence or in the presence of any anti-coagulants such as Elsevier's solution, potassium oxalate, ammonium oxalate, heparin, dextrose, etc.

In another embodiment the solvent used for removal of albumin and other low molecular weight proteins is saturated ammonium sulfate solution in the range of 15% to 40%.

In another embodiment the galactose binding proteins is removed by using any galactose containing glycoproteins such as asialo bovine submaxillary mucin, asialo sheep submaxillary mucin, asialo human chronic gonadotropin, asialo equine gastric mucin or hog gastric mucin etc. coupled with Sepharose or agarose as an affinity matrix.

In another embodiment the affinity matrix, for capturing O acetyl sialic acids specific fractions, used may be any available sialoglycoconjugates having terminal O acetyl sialic acids such as bovine submaxillary mucin or any gangliosides having terminal O acetyl sialic acids such as GD3.

In another embodiment the solvent used for eluting O acetyl sialic acids specific proteins may be a buffer selected from as ammonium hydroxide, borate buffer, carbonate bicarbonate buffer and ammonium bicarbonate buffer with high pH from 8 to 11 even expensive sugar such as O-acetylated sialic acid (as a monocaccharide or disaccharides or higher oligosaccharides with subterminal galactose of N acetyl galactosamine) may be used as eluting sugar. Molarity of buffer may be in the range of 0.02–0.5M.

In another embodiment neutralization may be carried out with sodium acetate or monosodium phosphate for better stability of the eluated protein. If sugars are used as eluting solution it may be removed simply by dialysis. Dialysis may be carried out at cold temperature between 4–25° C. for 24 to 72 hours to get disease specific antibody as a novel biomarker.

Accordingly, the present invention provides a disease specific antibody or immunoglobulin as biomarker by the process of present invention and used the same for diagnosis, monitoring outcome of treatment and prediction of relapse using a bovine submaxillary mucin-Enzyme linked immunosorbent assay (ELISA).

The novelty of this process is to capture the disease specific antibody as a novel biomarker specific for O-acetylated sialic acid by using bovine submaxillary mucin as an affinity matrix after careful removal of albumin, other low molecular weight fractions and galactose binding proteins from ALL serum. Characterization of this antibody as biomarker by several biochemical, immunochemical techniques it reveals that (i) biomarker is specific to leukemic blast cells in acute lymphoblastic leukemia (ii) irrespective of the lymphocytic origin of cancer cells such as acute lymphoblastic leukemia of B lymphocytes or acute lymphoblastic leukemia of T lymphocytes, this biomarker shows equal specificity, therefore, it may be considered as common biomarker and used for diagnosis of both types of acute lymphoblastic leukemia (iii) the amount of this biomarker specific for O-acetylated sialic acid is quantitated and has been exploited to correlate the status of patients with regard to their blast leukemic blast cells which stay in peripheral blood even after chemotherapy. The quantity of this disease specific antibody as the biomarker, specific for O-acetylated sialic acid, has been established to be directly proportional to presence of leukemic blast cells i.e., cancer cells, therefore, by simply measuring the amount of antibody as the biomarker by newly developed ELISA, it is possible to know the status of different stages of the disease (iv) thus its correlation with the status of the disease is assessed and confirmed that the disease specific antibody as the biomarker has both diagnostic and prognostic potential (v) The antibody i.e. immunoglobulin G (IgG) subclass distribution reacting with O-AcSA in comparison to antibody present in normal healthy individual has been characterized by the ELISA. Amongst the four human IgG subclasses, $IgG_1$, and $IgG_2$ are significantly increased in patients as compared to normal individuals. However, their $IgG_3$ and $IgG_4$ levels are unchanged and comparable to normal healthy individuals. Therefore, measuring both IgG1 and $IgG_2$ specific for O-Acetyl sialic acid in patients by an isotype ELISA is very much beneficial. The disease specific IgM antibody has also been found to be potentially important.

(a) By fluorescence activated cell sorter (FACS) analysis using flurescin (FITC) conjugated purified antibody, leukemia blasts show 50–90% binding. Both B and T blasts showed similar binding with FITC-antibody (leukemic purified disease specific antibody);

(b) In BSM-ELISA also Patient serum, both from B & T ALL Patient showed binding with BSM. Detection of this disease specific antibody as a biomarker specific for O-acetylated sialic acid, in patients serum has been carried out by bovine submaxillary mucin—ELISA for estimation of this antibody as a biomarker specific for O-acetylated sialic acid:

Preparation of Bovine Submaxillary Mucin

Bovine submaxillary mucin was prepared according to the method of Murphy & Gottschalk, Biochimica et Biophysica Acta, vol. 52, p 349, 1961. Briefly, tissues were homogenized and extracted thrice with an equal amount of water by centrifugation at 10,000 g for 15 minutes at 4° C. The supernatant was collected, pH adjusted to 4.5 and the resulting precipitate removed by centrifugation at 5000 g for 20 minutes. The supernatant was then neutralized (pH 6.0)

and dialyzed against water. Barium acetate was slowly added to the dialysate to make it 0.1 M followed by precooled methanol to give an alcohol concentration of 64% (v/v) and incubated overnight at 4° C. The precipitate formed was retrieved by centrifugation, dissolved in 0.1 M EDTA, dialyzed extensively against water and stored at −20° C. until use. Bovine submaxillary mucin and asialo-bovine submaxillary mucin were separately coupled to sepharose 4B using the method of Kohn and Wilchem. Asialo-bovine submaxillary mucin was prepared by acid hydrolysis of bovine submaxillary mucin with 0.05 M $H_2SO_4$ at 80° C. for one hour. De-O-acetylated Bovine submaxillary mucin was prepared by incubation with 0.2N NaOH for 45 minutes at 4° C. followed by immediate neutralization.

Bovine submaxillary mucin, having high percentage of 9-O-acetyl sialic acid, has been used to successfully capture a disease specific antibody as a biomarker, specific for O-acetylated sialic acid from the patients serum which in turn can be detected by horse radish peroxidase conjugated goat anti-human IgG and detected by using a substrate and optical density measured in an ELISA reader. Briefly, in bovine submaxillary mucin coated plate, wells were coated with bovine submaxillary mucin. Following three washes with buffer the wells were blocked. Purified antibody i.e., O-acetylated sialic acid specific biomarker or patient sera was incubated for some time at cold and its binding to the coating material was measured colorimetrically using horse radish peroxidase conjugated goat anti human antibodies and azino-bis thio-sulfonic acid as the substrate. The optical density was measured in an ELISA reader.

The amount of antibody as a biomarker, specific for O-acetylated sialic acid was determined and has been exploited to correlate the status of patients with regards to their blast cells which stay in peripheral blood even after chemotherapy. Thus, its correlation with the status of the disease was assessed.

The following examples are given by way of illustration of the present invention and therefore should not be construed to limit the scope of the present invention.

EXAMPLE 1

Approximately 2–3 ml of blood was collected from T-acute lymphoblastic (T-ALL)leukemia patients, blood was allowed to clot and the serum was separated by centrifugation.

Purification of a biomarker, the antibody specific for O-acetylated sialic acid: Patient serum (5 ml) pooled from two T-ALL patients containing 184 mg of total protein was used to purify the polyclonal antibody fraction with preferential affinity for O-AcSA. Briefly, 100% saturated solution of ammonium sulphate solution was added slowly to the patient's serum at 4° C. in such a way so that final concentration of ammonium sulphate in the solution become 33%. The solution was kept at cold for overnight for complete precipitation. Next day solution was centrifuged and dialyzed extensively against phosphate buffer saline to remove trace amount of ammonium sulphate fractionation. Now the total content of proteins is 138 mg. This protein (138 mg) was passed over an asialo-bovine submaxillary mucin— Sepharose 4B (3.6 mg/ml) column to remove galactose binding proteins. The galactose specific fractions remain bind to the column and unbound fractions do not have affinity for galactose. Therefore, they do not bind to the column. These unbound free fractions (70 mg) was then loaded onto an another column, namely bovine submaxillary mucin—Sepharose 4B column (5.7 mg/ml) which had been previously equilibrated with phosphate buffered saline (PBS, pH 7.2). Following removal of non-specifically bound proteins by extensive washings in PBS, specific protein was eluted with 0.1 M $NH_4OH$, pH11.0 and immediately neutralized with 0.2N acetic acid. The eluted protein fraction (4 mg) was then passed over a Protein G-agarose column (2 ml, Pierce), previously equilibrated with PBS, eluted with 0.1M citric acid from pH 6.5 was carried out and the fractions immediately neutralized with 2M Tris followed by extensive dialysis against PBS. The yield the biomarker of the invention, anti-O-acetyl sialic acid antibody, IgG1 was 0.140 mg.

The biological activity and affinity of this purified biomarker, specific for O-acetylated sialic acid was confirmed by bovine submaxillary mucin—ELISA and its specificity for O-acetylated sialic acids validated using de-O-acetylated Bovine submaxillary mucin a coating agent in bovine submaxillary mucin—ELISA.

EXAMPLE 2

The use of this biomarker for the diagnosis of acute lymphoblastic leukemia was carried out by developing a bovine submaxillary mucin—ELISA. Diagnosis of T-ALL:

In Bovine submaxillary mucin- ELISA, ELISA plate was coated with bovine submaxillary mucin (5 µg/ml, 100 µl/well) in 0.02M phosphate buffer, pH 7.4 and left it for overnight at 4° C. Following three washes with phosphate buffered saline (PBS) containing 0.1% Tween-20 (PBS-T), the wells were blocked with 2% bovine serum albumin for 2 hours at 25° C. Patient sera from T-ALL patients having 90% leukemic blasts or purified O-acetylated sialic acids specific antibody as a biomarker was incubated overnight at 4° C. in 1:10 dilutions and its binding to bovine submaxillary mucin was measured colorimetrically using horse radish peroxidase (HRP) conjugated protein A (1:5000, Sigma, St. Louis, Mo., USA) and azino-bis thio-sulfonic acid (ABTS) as the substrate.

EXAMPLE 3

Diagnosis of B-ALL by developing a bovine submaxillary mucin—ELISA

In Bovine submaxillary mucin—ELISA, ELISA plate was coated with bovine submaxillary mucin (5 µ/ml, 100 µl/well) in 0.02M phosphate buffer, pH 7.4 and left overnight at 4° C. Following three washes with phosphate buffered saline (PBS) containing 0.1% Tween-20 (PBS-T), the wells were blocked with 2% dry milk powder for 2 hours at 25° C. Patient from B ALL having 80% leukemic blasts or purified O-acetylated sialic acids specific antibody as the biomarker was incubated overnight at 4° C. in 1:10 dilutions and its binding to bovine submaxillary mucin was measured colorimetrically using horse radish peroxidase (HRP) conjugated goat anti human IgG1 (1:5000, Sigma, St. Louis, Mo., USA) and azino-bis thio-sulfonic acid (ABTS) as the substrate.

EXAMPLE 4

Diagnosis of ALL having both T and B leukemic blasts by developing a bovine submaxillary mucin ELISA In bovine submaxillary mucin—ELISA, ELISA plate was coated with bovine submaxillary mucin (5 µg/ml, 50 µl/well) in 0.02M phosphate buffer, pH 7.4 and left for 6 hours at 4° C. Following three washes with phosphate buffered saline (PBS) containing 0.1% Tween-20 (PBS-T), the wells were blocked with 2% bovine serum albumin for 1 hours at 37° C. Patient sera of mixed lineage having 80% leukemic blasts in both B and T lymphocytes or purified O-acetylated sialic acids specific biomarker was incubated overnight at 4° C. in 1:10 dilutions and its binding to bovine submaxillary mucin was measured calorimetrically using horse radish peroxidase (HRP) conjugated goat anti human IgG2 (1:5000, Sigma, St. Louis, Mo., USA) and azino-bis-sulfonic acid (ABTS) as the substrate.

EXAMPLE 5

Approximately 2–3 ml of blood was collected from B-acute lymphoblastic (B-ALL) leukemia patients, blood was allowed to clot and the serum was separated by centrifugation. 4 ml sera pooled from two B-ALL patients containing 170 mg of total protein was used to purify the biomarker. Briefly, 100% saturated solution of ammonium sulphate solution was added slowly to the patient's serum at 4° C. in such a way so that final concentration of ammonium sulphate in the solution become 30%. The solution was kept at cold for overnight for complete precipitation. Next day, solution was centrifuged and dialysed extensively against phosphate buffer saline to remove trace amount of ammonium sulphate fractionation. Now the total content of proteins is 120 mg. This protein (120 mg) was passed over an asialo- steep submaxillary mucin—Sepharose 4B (3.6 mg/ml) column to remove galactose binding proteins. The galactose specific fractions remain bind to the column and unbound fractions do not have affinity for galactose. Therefore, they do not bind to the column. These unbound free fractions (65 mg) was then loaded onto an another column, namely bovine submaxillary mucin—Sepharose 4B column (5.7 mg/ml) which had been previously equilibrated with phosphate buffered saline (PBS, pH 7.2). Following removal of non-specifically bound proteins by extensive washings in PBS, specific protein was eluted with 0.2M $NH_4OH$, pH 10.0 and immediately neutralized with 0.4N acetic acid. The eluted protein fraction (3 mg) was then passed over a Protein G-agarose column (1.50 ml), previously equilibrated with PBS, eluted with 0.1M citric acid from pH 3.5 was carried out and the fractions immediately neutralized with 2M Tris followed by extensive dialysis against PBS. The yield of the product, biomarker, anti-O-acetyl sialic acid antibody, IgG2, was 0.125 mg.

EXAMPLE 6

Approximately 2–3 ml of blood was collected from mixed lineage B&T-acute lymphoblastic leukemia patients, blood was allowed to clot and the serum was separated by centrifugation, 4 ml sera pooled from two patients containing 165 mg of total protein was used to purify the biomarker. Briefly, 100% saturated solution of ammonium sulphate solution was added slowly to the patient's serum at 4° C. in such a way so that final concentration of ammonium sulphate in the solution become 40%. The solution was kept at cold for overnight for complete precipitation. Next day solution was centrifuged and dialyzed extensively against phosphate buffer saline to remove trace amount of ammonium sulphate fractionation. Now the total content of proteins is 130 mg. This protein (130 mg) was passed over an asialo-bovine submaxillary mucin—Sepharose 4B (3.6 mg/ml) column to remove galactose binding proteins. The galactose specific fractions remain bound to the column and unbound fractions do not have affinity for galactose. Therefore, they do not bind to the column. These unbound free fractions (60 mg) were then loaded onto an another column, namely bovine submaxillary mucin—Sepharose 4B column (5.7 mg/ml) which had been previously equilibrated with phosphate buffered saline (PBS, pH 7.2). Following removal of non-specifically bound proteins by extensive washings in PBS, specific protein was eluted with 0.05 M $NH_4OH$, pH 11 and immediately neutralized with 0.15N acetic acid. The eluted protein fraction (3.5 mg) was then passed over a Protein A-agarose column (2 ml, Pierce), previously equilibrated with PBS, eluted with glycin HCl buffer pH 2.5 and the fractions immediately neutralized with 1M Tris followed by extensive dialysis against PBS. The yield of the biomarker, anti-O-acetyl sialic acid antibody, was 0.140 mg.

EXAMPLE 7

Approximately, 5 ml of blood was collected from normal human volunteers and the serum was separated by centrifugation. Crude serum (80 mg) following a 33% ammonium sulphate fractionation (55 mg) was passed over an asialo-bovine submaxillary mucin—Sepharose 4B (3.6 mg/ml) column to remove galactose binding proteins. The resulting eluate (10 mg) was then loaded onto a bovine submaxillary mucin—Sepharose 4B column (5.7 mg/ml) which had been previously equilibrated with phosphate buffered saline. Following removal of non-specifically bound proteins by extensive washings in PBS, specific protein was eluted with 0.1M $NH_4OH$, pH 11.0 and immediately neutralized with 0.2N acetic acid. The yield of this O-acetylated sialic acids specific biomarker was 10 fold less than ALL serum. The eluted protein (0.4 mg) fraction was then passed over a Protein G-agarose column, previously equilibrated with PBS, eluted with 0.1M citric acid, pH 2.5 followed by immediate neutralization with 2M Tris and extensively dialysed against PBS. No significant amount of biomarker could be detected.

EXAMPLE 8

Approximately 5 ml of blood was collected separately from five different blood related diseases (Non hodgkin lymphoma, Chronic Myloblastic Leukemic, Acute Myloblastic Leukemic, Thalassemmia and Aplastic Anemia) served as negative controls and the serum was separated by centrifugation and processed separately for purification of O-acetylated sialic acids specific antibody as biomarker (if any). Serum following fractionation 33% ammonium sulphate was passed over an asialo-bovine submaxillary mucin—Sepharose 4B (3.6 mg/ml) column. The unbound fraction was then loaded onto a bovine submaxillary mucin—Sepharose 4B column (5.7 mg/ml) in phosphate buffered saline. Following removal of non-specifically bound proteins by extensive washings in PBS, No specific protein could be eluted with 0.1M $NH_4OH$, pH 11.0. Therefore, O-acetylated sialic acids specific antibody as biomarker is absent in these patients.

EXAMPLE 9

The use of this biomarker for the diagnosis of acute lymphobiastic leukemia was carried out by developing a bovine submaxillary mucin—ELISA. Diagnosis of T-ALL in Bovine submaxillary mucin—ELISA ELISA plate was coated with bovine submaxillary mucin (5 μg/ml, 100μl/well) in 0.02M phosphate buffer, pH 7.4 and left it for overnight at 4° C. Following three washes with phosphate buffered saline (PBS) containing 0.1% Tween-20 (PBS-T), the wells were blocked with 2% bovine serum albumin for 2 hours at 25° C. Patient sera from T ALL patients having 90% leukemic blasts or purified O-acetylated sialic acids specific antibody as the biomarker was incubated overnight at 4° C. in 1:10 dilutions and its binding to bovine submaxillary mucin was measured colorimetrically using horse radish peroxidase (HRP) conjugated protein A (1:5000, Sigma, St. Louis, Mo., USA) and azino-bis thio-sulfonic acid (ABTS) as the substrate.

EXAMPLE 10
Diagnosis of B-ALL by developing a bovine submaxillary mucin—ELISA In bovine submaxillary mucin—ELISA, ELISA plate was coated with bovine submaxillary mucin (5 µg/ml, 100 µl/well) in 0.02M phosphate buffer, pH 7.4 and left it overnight at 4° C. Following three washed with phosphated saline (PBS) containing 0.1% Tween-20 (PBS-T), the wells were blocked with 2% dry milk powder for 2 hours at 25° C. Patient from B ALL having 80% leukemic blasts or purified O-acetylated sialic acids specific biomarker was incubated overnight at 4° C. in 1:10 dilutions and its binding to bovine submaxillary mucin was measured calorimetrically using horse radish peroxidase (HRP) conjugated goat anti human IgG1 (1:5000, Sigma, St. Louis, Mo., USA) and azino-bis thio-sulfonic acid (ABTS) as the substrate.

EXAMPLE 11
Diagnosis of ALL having both T and B leukemic blasts by developing a bovine submaxillary mucin—ELISA In bovine submaxillary mucin—ELISA, ELISA plate was coated with bovine submaxillary mucin (5 µl/well) in 0.02M phosphate buffer, pH 7.4 and left for 6 hours at 4° C. Following three washes with phosphate buffered saline (PBS) containing 0. 1% Tween-20 (PB S-T)m the wells were blocked with 2% bovine serum albumin for 1 hours at 37° C. Patient sera of mixed lineage having 80% leukemic blasts in both B and T lymphocytes or purified O-acetylated sialic acids specific antibody as the biomarker was incubated overnight at 4° C. in 1:10 dilutions and its binding to bovine submaxillary mucin was measured calorimetrically using horse radish perodixase (HRP) conjugated goat anti human IgG2 (1:5000, Sigma, St. Louis, Mo., USA) and azino-bis thio-sulfonic acid (ABTS) as the substrate. An EXAMPLE for monitoring and prediction of relapse:

BSM-ELISA was carried out as shown in above Examples with a patient who has been monitored for last 4–5 years and whose relapse can be predicted as shown in Table 4.

Results of Individual Patients

Study included human blood samples n=187; 124 in India & 63 in UK. All these patients were divided according to their duration of treatment. Serum from all these patients were collected and tested by our newly invented BSM-ELISA. Results are expressed in the measurement of optical density (O.D) at 405 nm using a ELISA reader, as shown in tables 1 & 2 hereinbelow:

TABLE 1

PHASE A (0–4 weeks treatment/first remission)

| Patient No. | Sex, Age (Year) | Treatment (weeks) | Peripheral blast Cell (%) | O.D at 405 nm |
|---|---|---|---|---|
| 1. | M,4.5 | 0 | 80 | 2.96 |
| 2 | M,5 | 0 | 80 | 2.8 |
| 3 | M,5 | 0 | 65 | 2.02 |
| 4 | M,7.5 | 0 | 70 | 2.134 |
| 5 | M,8 | 0 | 86 | 2.92 |
| 6 | M,5 | 0 | 80 | 2.85 |
| 7 | M,5 | 0 | 90 | 2.87 |
| 8 | M,5 | 0 | 72 | 2.16 |
| 9 | M,4 | 0 | 74 | 2.48 |

TABLE 1-continued

PHASE A (0–4 weeks treatment/first remission)

| Patient No. | Sex, Age (Year) | Treatment (weeks) | Peripheral blast Cell (%) | O.D at 405 nm |
|---|---|---|---|---|
| 10 | M,2.5 | 0 | 92 | 3.01 |
| 11 | M,2.5 | 0 | 80 | 3.14 |
| 12 | M,6 | 0 | 82 | 3.15 |
| 13 | F,5 | 0 | 90 | 2.35 |
| 14 | M,4 | 0 | 68 | 2.11 |
| 15 | M,5 | 0 | 92 | 2.86 |
| 16 | M,3 | 0 | 80 | 2.36 |
| 17 | M,7 | 0 | 78 | 2.5 |
| 18 | M,6 | 0 | 74 | 2.2 |
| 19 | M,6 | 0 | 70 | 2.44 |
| 20 | M,5 | 0 | 80 | 2.84 |
| 21 | M,3.5 | 0 | 76 | 2.46 |
| 22 | M,6 | 0 | 74 | 2.35 |
| 23 | M,6 | 0 | 72 | 2.4 |
| 24 | F,11 | 0 | 90 | 3 |
| 25 | F,7.5 | 0 | 78 | 2.8 |
| 26 | M,3 | 0 | 80 | 2.81 |
| 27 | M,5 | 0 | 78 | 2.68 |
| 28 | M,3.5 | 0 | 76 | 2.58 |
| 29 | F,8 | 0 | 68 | 2.46 |
| 30 | F,7.5 | 0 | 80 | 2.54 |
| 31 | M,8 | 0 | 86 | 2.86 |
| 32 | M,3.5 | 0 | 86 | 2.74 |
| 33 | M,6 | 0 | 90 | 2.86 |
| 34 | M,1.5 | 0 | 67 | 2.06 |
| 35 | F,7.5 | 0 | 68 | 2.04 |
| 36 | M,4 | 0 | 66 | 2 |
| 37 | M,6 | 0 | 68 | 2.1 |
| 38 | M,4.5 | 0 | 71 | 2.4 |
| 39 | M,6 | 0 | 76 | 2.54 |
| 40 | M,4 | 0 | 78 | 2.62 |
| 41 | M,6 | 0 | 92 | 3.1 |

RESULT: Phase A comprised of 41 ALL patients. The mean O.D.±S.E. of clinically diagnosed ALL sera was 2.53±0.07 reflecting a significantly high level of anti-9-OacsG antibody in serum of patients during Phase A. Individual anti-OacSA antibody concentration as determined by the BSM-ELISA showed a good correlation with the percentage of peripheral blast cells ($r^2$=0.84). A blast cell % of 78.12±7.97 was observed in Phase A. Therefore the O.D. at 405 nm obtained by BSM-ELISA bears a direct relationship with the present of blast cells. The level of antibody, as indicated by the O.D. at 405 nm, serves as a direct reflection of % blast cells i.e. acuteness of the disease. Thus ALL could be diagnosed by this invented process. Using the mean O.D.+3 S.D. of normal human serum as the cut off value for a positive result sera from 41/41 (100%) were positive.

TABLE 2

Diagnosis of ALL patients, Normal donors and patients with other hematological diseases showed 7–8 times less OD value.

| ALL (Phase-A) (n = 41) | NORMAL DONORS (n = 25) | AML (n = 17) | CML (n = 6) | CLL (n = 7) | NHL (n = 2) |
|---|---|---|---|---|---|
| 2.96 | 0.35. | 0.281 | 0.286 | 0.216 | 0.246 |
| 2.8 | 0.301 | 0.299 | 0.301 | 0.208 | 0.231 |
| 2.02 | 0.326 | 0.35 | 0.262 | 0.234 | |
| 2.134 | 0.337 | 0.31 | 0.258 | 0.236 | |
| 2.92 | 0.366 | 0.35 | 0.292 | 0.218 | |
| 2.85 | 0.414 | 0.22 | 0.288 | 0.254 | |
| 2.87 | 0.369 | 0.29 | | 0.268 | |
| 2.16 | 0.321 | 0.2 | | | |
| 2.48 | 0.375 | 0.2 | | | |

TABLE 2-continued

Diagnosis of ALL patients, Normal donors and patients with other hematological diseases showed 7–8 times less OD value.

| ALL (Phase-A) (n = 41) | NORMAL DONORS (n = 25) | AML (n = 17) | CML (n = 6) | CLL (n = 7) | NHL (n = 2) |
|---|---|---|---|---|---|
| 3.01 | 0.379 | 0.28 | | | |
| 3.14 | 0.375 | 0.34 | | | |
| 3.15 | 0.4 | 0.29 | | | |
| 2.35 | 0.4 | 0.28 | | | |
| 2.11 | 0.45 | 0.26 | | | |
| 2.86 | 0.321 | 0.27 | | | |
| 2.36 | 0.302 | 0.28 | | | |
| 2.5 | 0.314 | 0.28 | | | |
| 2.2 | 0.329 | | | | |
| 2.44 | 0.328 | | | | |
| 2.84 | 0.321 | | | | |
| 2.46 | 0.302 | | | | |
| 2.35 | 0.304 | | | | |
| 2.4 | 0.342 | | | | |
| 3 | 0.302 | | | | |
| 2.48 | 0.308 | | | | |
| 2.81 | | | | | |
| 2.68 | | | | | |
| 2.58 | | | | | |
| 2.46 | | | | | |
| 2.54 | | | | | |
| 2.86 | | | | | |
| 2.74 | | | | | |
| 2.86 | | | | | |
| 2.06 | | | | | |
| 2.04 | | | | | |
| 2 | | | | | |
| 2.1 | | | | | |
| 2.4 | | | | | |
| 2.54 | | | | | |
| 2.62 | | | | | |
| 3.1 | | | | | |

RESULT: No cross reactivity was observed with sera of CML, CLL, AML and NHL patients where antibody levels were lesser than normal human serum (NHS) from 25 normal human volunteers of different ages, having different blood groups were included in study. The mean on the OD was 0.341±0.007, reflecting a very low level of antibody titre on serum of normal donors as compared to ALL patients. In AML (Acute Myelogenous Leukemia), CML (Chronic Myelogenous Leukermia), CLL(Chronic Lymphocytic Leukemia), NHL (Non Hodgkin's Lymphoma) level of antibody titre was lesser than that of the normal human donors. Thus patients of other diseases (AML, CML, CLL, NHL) served as negative controls showing no cross reactivity with ALL by this invented process.

TABLE 3

Difference in antibody level in different phase of ALL

| PHASE-A (n = 41) | PHASE-B (n = 7) | PHASE-C (n = 5) | PHASE-D (n = 10) | PHASE-E (n = 4) |
|---|---|---|---|---|
| 2.96 | 1.58 | 0.908 | 0.705 | 2.3 |
| 2.8 | 1.404 | 0.92 | 0.729 | 2.12 |
| 2.02 | 1.601 | 1.028 | 0.612 | 1.98 |
| 2.134 | 1.65 | 0.969 | 0.61 | 2.18 |
| 2.92 | 1.44 | 0.996 | 0.606 | |
| 2.85 | 1.57 | | 0.609 | |
| 2.87 | 1.67 | | 0.668 | |
| 2.16 | | | 0.622 | |
| 2.48 | | | 0.687 | |
| 3.01 | | | 0.649 | |
| 3.14 | | | | |
| 3.15 | | | | |
| 2.35 | | | | |
| 2.11 | | | | |
| 2.86 | | | | |
| 2.36 | | | | |
| 2.5 | | | | |
| 2.2 | | | | |
| 2.44 | | | | |
| 2.84 | | | | |
| 2.46 | | | | |
| 2.35 | | | | |
| 2.4 | | | | |
| 3 | | | | |
| 2.48 | | | | |
| 2.81 | | | | |
| 2.68 | | | | |
| 2.58 | | | | |
| 2.46 | | | | |
| 2.54 | | | | |
| 2.86 | | | | |
| 2.74 | | | | |
| 2.86 | | | | |
| 2.06 | | | | |
| 2.04 | | | | |
| 2 | | | | |
| 2.1 | | | | |
| 2.4 | | | | |
| 2.54 | | | | |
| 2.62 | | | | |
| 3.1 | | | | |

RESULT: Phase A, B, C, D comprised of 67 ALL patients and the "level of antibody titre" (X±SE) decreased to 0.65±0.05 reflecting a decline in the antibody titer. The different between the 'level of antibody titre' in Phase A and Phase B was statistically significant (p<0.0005). Thus chemosensitivity of ALL patients could be detected by this invented process. Phase B comprised of 7 ALL patients and the 'level of antibody titre' (X±SE) decreased to 1.56±0.11 and was statistically significant (p<0.006). Phase C included 5 ALL patients. The mean (X±SE) of 'level of antibody titre' was 0.96±0.05. However, it must be noted that although no blast cells could be detected by available methods, the 'level of antibody titre', even in maintenance therapy, was significantly high as compared to normal donors (Table 2). Therefore, the 'level of antibody titre' in maintenance therapy is significantly higher than normal donors. Thus the 'level of antibody titre' serves as direct reflection of blast cell %. Minimal residual disease (MRD) can be detected by this invented process. Phase D included 10 patients who were followed up after completion of maintenance therapy. The mean (X±SE) of the 'level of antibody titre' was 0.65±0.05 (Table 2) reflecting the persistence of antibody level. Thus MRD could be detected by this invented process. In summary, the antibody titre significantly decreased from phase A to phase B (2.6±0.45 vs 1.56±0.11 p<0.01), phase B to Phase C (1.56+0.11 vs 0.96±0.05, p<0.05), Phase C to Phase D (0.96±0.05 vs 0.65±0.05, p<0.05)

RELAPSE CASES (patients for which relapse could be successfully predicted by our invented assay), The antibody titre significantly increased with relapse from Phase D to Phase E (0.65±0.05 vs. 2.14±0.13 p<0.01). From the increased O.D at 405 nm as compared to that required during maintenance therapy and follow-up the applicants could predict relapse in these patients. The prediction correlated well with the clinical observation.

TABLE 4

A representative profile of a patient, age 3 years, sex: male who has been followed up after completion of maintenance therapy for 4.5 years in which relapse was successfully predicted by our invented assay.

|         | BLAST(%) | O.D at 405 nm |
|---------|----------|---------------|
| PHASE-A | 90       | 2.876         |
| PHASE-B | 5        | 1.5           |
| PHASE-C | <5       | 0.908         |
| PHASE-D | <5       | 0.622         |
| PHASE-E | 80       | 2.3           |

RESULT: It was interesting that the single patient in this study who relapsed showed a dramatic increase in antibody levels against O-AcSA. From the increased O.D. at 405 nm as compared to that required during maintenance therapy and follow-up (Table 3) we could predict relapse in this patient. Our prediction correlated well with the clinical observation.

A study was also completed in the LRF Molecular Pharmacology Specialist Programme, Cancer Research Unit, Medical School, Newcastle Upon Tyne, U.K.

Results are tabulated below which clearly indicated that increased antibody levels occur in ALL patients and a good correlation observed with anti-OacSA antibody titres in ALL patients (n=59) with chemotherapeutic response.

Serum from clinically diagnosed and immunophenotypically confirmed. ALL patients were collected at the following time points (Table 5) along with normal healthy donors (n=4).

TABLE 5

| Phase of treatment | Weeks of treatment | No. |
|--------------------|--------------------|-----|
| A | At diagnosis | 11 |
| B | wk. 15–20; wk 26–35 | 10 |
| C | wk. 26–35 | 23 |
| D | wk. 85–100 | 10 |
| E | 306 months, Following completion of Chemotherapy | 4 |
| F | Relapse | 1 |

| Phase of treatment | No. | Mean O.D (405 nm) ± S.E |
|--------------------|-----|--------------------------|
| A | 11 | 2.95 ± 0.7 |
| B | 10 | 1.0 ± 0.27 |
| C | 23 | 0.6 ± 0.16 |
| D | 10 | 0.62 ± 0.2 |
| E | 4  | 0.4 ± 0.15 |
| F | 1  | 0.91 |

These results clearly indicate that a dramatic increase in antibody levels directed against O-AcSA occurs in ALL patients at presentation as compared to normal healthy individual whose mean O.D±S.D was only 0.3±0.02. With response to chemotherapy, there was a significant decrease in anti O-AcSA antibody levels (p<0.0008) which interestingly increased in patients who relapsed. Therefore, BSM-ELISA can predict impending relapse.

The main advantages of the present invention are:
1. To provide a reagent, a disease specific antibody as a novel biomarker specific for O-acetylated sialic acid, by simple process with a significant high yield.
2. The reagent has an amplified biological potency to bind with cancer cells, therefore, it has tremendous potential in terms of its detection capability of ALL patients under different phases of treatment e.g. Potential for diagnosis and prognosis of ALL patients.
3. Furthermore, the process for purification of a biomarker specific for O-acetylated sialic acid is not a complicated one and comprises only a few simple setups including removal of other non O-acetylated proteins by using asialo bovine submaxillary mucin affinity column followed by capturing novel O-acetylated sialic acid specific biomarker using a bovine submaxillary mucin—Sepharose column. Thus, this disease specific antibody as a novel biomarker, specific for O-acetylated sialic acid purified from these patient's serum is of significant and maximum potency in detecting ALL patients under different phases of treatment i.e., detection of minimal residual disease in ALL, which is a challenging problem for leukemia specialist.
4. To provide a reagent by a process with a significant commercial application and predict relapse.
5. For diagnosis of ALL patients of different lineages e.g., T cell ALL, B cell ALL and mixed lineage ALL having cancer in both B and T lymphocytes by this O-acetylated sialic acid specific antibody reflecting its general expression.
6. It can distinguish between different stages of acute lymphoblastic leukemia which correlate well with the clinical status of the disease.
7. It detects the extent to which the patient has responded to chemotherapy.
8. Serum from other hematological disorder do not possess this biomarker.
9. Normal human serum contain very insignificant amount of this biomarker.

Example embodiments of the present invention have now been described in accordance with the above advantages. It will be appreciated that these examples are merely illustrative of the invention. Many variations and modifications will be apparent to those skilled in the art.

What is claimed is:

1. A novel process for preparation of O-acetyl specific immunoglobulins as a biomarker specific for O-acetylated sialic acid for diagnosing, monitoring treatment outcome and predicting relapse of acute lymphoblastic leukemia, said process comprising the steps of:
   (i) separating serum from whole blood from a patient suffering from acute lymphoblastic leukemia;
   (ii) removing galactose-binding proteins from said serum by column chromatography on an asialo-bovine submaxillary mucin affinity matrix;
   (iii) collecting the unbound galactose-free protein fraction from the affinity matrix;
   (iv) passing said galactose-free protein fraction over another affinity matrix having terminal O-acetyl sialic acid moiety to capture the O-acetyl sialic acid specific protein fraction;
   (v) eluting the O-acetyl sialic acid specific protein fraction with a buffer at alkaline pH in the range of about 8.0–11.0 followed by neutralization of said fraction; and
   (vi) purifying from the O-acetyl sialic acid specific protein fraction, the O-acetyl sialic acid specific immunoglobulins.

2. The process as claimed in claim 1, wherein the immunoglobulins specific for O-acetylated sialic acid are purified from the serum of patients suffering from acute lymphoblastic leukemia at different stages of the disease.

3. The process as claimed in claim 1, wherein the whole blood is collected in a container in the presence or absence of an anticoagulant.

4. The process as claimed in claim 1, wherein the whole blood is incubated for clotting at room temperature, or plasma is collected from the blood.

5. The process as claimed in claim 1, wherein the O-acetyl sialic acid specific protein fraction is neutralized with sodium acetate or monosodium phosphate to stabilize the eluted protein fraction.

6. The process as claimed in claim 1, wherein purifying the O-acetyl sialic acid specific immunoglobulins comprises utilizing a column selected from the group consisting of Protein G-agarose, Protein A-agarose, anti-human immunoglobulin and IgG/IgM coupled to agarose.

7. The process as claimed in claim 1, wherein said immunoglobulins are eluted with a buffer at pH in the range of 2.0–6.5 and neutralized for stabilization.

8. The process as claimed in claim 1, further comprising purifying the neutralized immunoglobulins by dialysis.

9. A method for diagnosing, monitoring treatment outcome and predicting relapse of acute lymphoblastic leukemia comprising the steps of:

(i) separating serum from whole blood from a patient suffering from acute lymphoblastic leukemia;

(ii) removing galactose-binding proteins from said serum by column chromatography on an asialo-bovine submaxillary mucin affinity matrix;

(iii) collecting the unbound galactose-free protein fraction from the affinity matrix;

(iv) passing said galactose-free protein fraction over another affinity matrix having terminal O-acetyl sialic acid moiety to capture the O-acetyl sialic acid specific protein fraction;

(v) eluting the O-acetyl sialic acid specific protein fraction with a buffer at alkaline pH in the range of about 8.0–11.0 followed by neutralization of said fraction; and (vi) passing said O-acetyl sialic acid specific protein fraction over a column selected from the group consisting of Protein G-agarose, Protein A-agarose, anti-human immunoglobulin, and IgG/IgM coupled to agarose;

(vii) purifying from the O-acetyl sialic acid specific protein fraction, the O-acetyl sialic acid specific immunoglobulins;

(viii) determining the quantity of purified O-acetyl sialic acid specific immunoglobulins from said patient by an immunodetection assay wherein a decrease in the immunoglobulin level is indicative of a chemotherapeutic response and an increase in said immunoglobulin level is indicative of a relapse of acute lymphoblastic leukemia.

10. The method as claimed in claim 9, wherein the whole blood is collected in a container in the presence or absence of an anticoagulant.

11. The method as claimed in claim 9, wherein the whole blood is incubated for clotting at room temperature, or plasma is collected from the blood.

12. The method as claimed in claim 9, wherein the O-acetyl sialic acid specific protein fraction is neutralized with sodium acetate or monosodium phosphate to stabilize the eluted protein fraction.

13. The method as claimed in claim 9, wherein the purified O-acetyl sialic acid specific immunoglobulins from said patient are determined by an isotype ELISA to diagnose phases or stages of acute lymphoblastic leukemia, wherein the quantity of said immunoglobulins is directly proportional to the presence of leukemic blast cells.

* * * * *